United States Patent
Bae et al.

(10) Patent No.: US 10,493,100 B2
(45) Date of Patent: Dec. 3, 2019

(54) PHARMACEUTICAL COMPOSITION FOR PREVENTING OR TREATING BRAIN CANCER INCLUDING CRYSTAL POLYMORPH OF TETRAARSENIC HEXOXIDE, AND METHOD FOR PREPARING SAME

(71) Applicant: CHEMAS CO., LTD., Seoul (KR)

(72) Inventors: Ill Ju Bae, Gangwon-do (KR); Zenglin Lian, Beijing (CN)

(73) Assignee: CHEMAS CO., LTD., Seoul (KR)

( * ) Notice: Subject to any disclaimer, the term of this patent is extended or adjusted under 35 U.S.C. 154(b) by 0 days.

(21) Appl. No.: 16/461,892

(22) PCT Filed: Sep. 7, 2017

(86) PCT No.: PCT/KR2017/009820
§ 371 (c)(1),
(2) Date: May 17, 2019

(87) PCT Pub. No.: WO2018/093029
PCT Pub. Date: May 24, 2018

(65) Prior Publication Data
US 2019/0328779 A1 Oct. 31, 2019

(30) Foreign Application Priority Data
Nov. 18, 2016 (KR) ........................ 10-2016-0154409

(51) Int. Cl.
*A61K 33/36* (2006.01)
*A61P 35/04* (2006.01)

(52) U.S. Cl.
CPC .............. *A61K 33/36* (2013.01); *A61P 35/04* (2018.01)

(58) Field of Classification Search
None
See application file for complete search history.

(56) References Cited

U.S. PATENT DOCUMENTS

2002/0028253 A1   3/2002   Bae et al.

FOREIGN PATENT DOCUMENTS

| KR | 10-0272835 B1    | 11/2000 |
|----|------------------|---------|
| KR | 10-2010-0054210 A | 5/2010  |
| KR | 10-1119587 B1    | 4/2012  |
| KR | 10-1755556 B1    | 7/2017  |

OTHER PUBLICATIONS

International Search report issued for International Application No. PCT/KR2017/009820 dated Dec. 20, 2017, 4 pages.
Gwak, H. S., "Tetraarsenic oxide-induced inhibition of malignant glioma cell invasion in vitro via a decrease in matrix metalloproteinase secretion and protein kinase B phosphorylation", J. Neurosurg, vol. 121, pp. 1483-1491, 2014, 9 pages.

*Primary Examiner* — Jeffrey T. Palenik
(74) *Attorney, Agent, or Firm* — Rothwell Figg Ernst & Manbeck P.C.

(57) ABSTRACT

The present invention relates to a pharmaceutical composition which is for preventing or treating brain cancer and includes at least 99% of a crystal polymorph of tetraarsenic hexoxide a ($As_4O_6$-a), and to a method for preparing same. A composition according to the present invention exhibits excellent cancer cell proliferation inhibition and metastasis inhibition effects, and thus may be usefully used as an anti-cancer agent.

5 Claims, 8 Drawing Sheets

PHARMACEUTICAL COMPOSITION FOR PREVENTING OR TREATING BRAIN CANCER INCLUDING CRYSTAL POLYMORPH OF TETRAARSENIC HEXOXIDE, AND METHOD FOR PREPARING SAME

CROSS-REFERENCE TO RELATED APPLICATIONS

The application is a 35 U.S.C. § 371 National Phase Entry Application from PCT/KR2017/009820, filed on Sep. 7, 2017, which claims the benefit of Korean Patent Application No. 10-2016-0154409 filed on Nov. 18, 2016, the disclosures of which are incorporated herein in their entirety by reference.

TECHNICAL FIELD

The present invention relates to a pharmaceutical composition containing a crystalline polymorph of tetraarsenic hexoxide for prevention or treatment of brain cancer.

BACKGROUND ART

Cancer is characterized by uncontrolled cell growth, and such abnormal cell growth forms a mass of cells called a tumor, which penetrates into surrounding tissues, and, in severe cases, causes metastasis into other organs of the body. Academically, tumors are called neoplasia. Cancer affects all tissues and organs of the body at various prevalence rates.

Especially, brain cancer (malignant brain tumor) causes great damage to the brain, and the survival rate of brain cancer patients is very low. Surgical excision is most effective in existing therapies for brain cancer. However, in many cases, surgery is impossible depending on the type or location of brain cancer, and complete excision results in a very high risk of postoperative complications. In addition, the brain has brain-blood barrier (BBB) that suppresses the penetration of drugs, and thus in order to treat brain cancer through chemotherapy using anticancer drugs, a higher concentration of anticancer drugs compared with other cancers needs to be administered, causing serious side effects in the other organs of the body.

Therefore, with respect to the treatment of brain cancer, there is a continuing need for therapeutic agents having excellent anticancer effects and no difficulty in passing through BBB.

The present inventors have already received patent rights of technical features wherein tetraarsenic hexoxide purified from natural arsenolite containing arsenic through separation and purification techniques showed cancer metastasis suppressing effects in animal experiments and had excellent anticancer treatment effects when administered to end-stage cancer patients with uterine cancer, bladder cancer, lung cancer, maxillary sinus cancer, kidney cancer, and the like (Korean Patent No. 272835).

The present inventors, as a result of continuous research on arsenic, revealed that tetraarsenic hexoxide having 99% or more of tetraarsenic hexoxide crystalline polymorph a can be produced by a novel preparation method, different from the method disclosed in the above registered patent, and a composition containing such tetraarsenic hexoxide has a remarkable effect on brain cancer prevention or treatment, and completed the present invention.

Meanwhile, it has been previously reported that tetraarsenic hexoxide induced the inhibition of malignant glioma cell invasion (J Neurosurg 121: 1483-1491, 2014), but this literature does not disclose what type of crystalline polymorph the tetraarsenic hexoxide has, and it was verified that a composition containing 99% or more of tetraarsenic hexoxide crystalline polymorph a, prepared by the preparation method of the present invention, had a better brain cancer treatment effect than the tetraarsenic hexoxide disclosed in the above literature.

DETAILED DESCRIPTION OF THE INVENTION

Technical Problem

An aspect of the present invention is to provide a pharmaceutical composition containing a crystalline polymorph of tetraarsenic hexoxide ($As_4O_6$) as an active ingredient for prevention or treatment of brain cancer.

Another aspect of the present invention is to provide a method for preparing a pharmaceutical composition containing a crystalline polymorph of tetraarsenic hexoxide ($As_4O_6$) as an active ingredient for prevention or treatment of brain cancer.

Technical Solution

The present invention is directed to a pharmaceutical composition for prevention or treatment of brain cancer, the pharmaceutical composition containing a crystalline polymorph of tetraarsenic hexoxide ($As_4O_6$), wherein the tetraarsenic hexoxide includes 99% or more of tetraarsenic hexoxide crystalline polymorph a ($As_4O_6$-a).

The tetraarsenic hexoxide of the composition may include less than 1% of tetraarsenic hexoxide crystalline polymorph b ($As_4O_6$-b).

The tetraarsenic hexoxide may have a purity of 99.9% or more.

The $As_4O_6$-a and $As_4O_6$-b may have features (i) to (iii) below.

TABLE 1

| Category | Crystalline polymorph a ($As_4O_6$-a) | Crystalline polymorph b ($As_4O_6$-b) |
| --- | --- | --- |
| (i) Cell parameters | $a = b = c = 11.0734$ Å<br>$\alpha = \beta = \gamma = 90°$<br>$V = 1357.82$ Å$^3$ | $a = b = c = 11.0600$ Å<br>$\alpha = \beta = \gamma = 90°$<br>$V = 1352.90$ Å$^3$ |
| (ii) As—O bond length | 1.786 Å | 2.011 Å |
| (iii) O—As—O bond angle | 98.36° | 109.47° |

The $As_4O_6$-a has a crystal form, of which the X-ray powder diffraction spectrum obtained by using a light source wavelength of 1.5406 □ within a diffraction angle (2θ) of 10° to 50° at a rate of 1°/min (scan step of 0.02°) shows peaks at 2θ values of 13.84, 27.88, 32.32, 35.3, 39.84, 42.38, 46.34, 48.6, and 49.34 (see FIG. 1). In addition, the ratio of main peaks shown at 2θ values of 13.8 and 27.9 is 1:1.3.

The $As_4O_6$-b has a crystal form, of which the X-ray powder diffraction spectrum obtained by using a light source wavelength of 1.5406 □ within a diffraction angle (2θ) of 10° to 50° at a rate of 1°/min (scan step of 0.02°) shows peaks at 2θ values of 13.86, 27.92, 32.36, 35.34, 39.9, 42.44, 46.4, 48.66, and 49.4 (see FIG. 1). In addition, the ratio of main peaks shown at 2θ values of 13.8 and 27.9 is 1:2.5.

In accordance with another aspect of the present invention, there is provided a pharmaceutical composition containing a crystalline polymorph of tetraarsenic hexoxide ($As_4O_6$) as an active ingredient for inhibition of brain cancer metastasis, wherein the tetraarsenic hexoxide includes 99% or more of tetraarsenic hexoxide crystalline polymorph a.

In accordance with another aspect of the present invention, there is provided a method for preparing a pharmaceutical composition containing a crystalline polymorph of tetraarsenic hexoxide ($As_4O_6$) as an active ingredient for prevention or treatment of brain cancer, the method including:

a first step of heating sodium chloride at 100~800° C., followed by cooling;

a second step of placing arsenic trioxide ($As_2O_3$) on the sodium chloride, followed by heating from 100° C. to 1000° C. in an airtight state and then cooling;

a third step of separating crystals crystallized in a filter bed; and a fourth step of repeating the second and third steps four to ten times using the crystals obtained in the third step instead of the arsenic trioxide in the second step, thereby obtaining tetraarsenic hexoxide crystals, wherein the tetraarsenic hexoxide crystals obtained in the fourth step includes 99% or more of tetraarsenic hexoxide crystalline polymorph a ($As_4O_6$-a).

Hereinafter, the present invention will be described in more detail.

The present invention is directed to a pharmaceutical composition containing tetraarsenic hexoxide ($As_4O_6$) as an active ingredient for prevention or treatment of brain cancer, the tetraarsenic hexoxide including 99% or more of tetraarsenic hexoxide crystalline polymorph a ($As_4O_6$-a).

The method for preparing a composition for prevention or treatment of brain cancer of the present invention includes: a first step of heating sodium chloride at 100~800° C., followed by cooling; a second step of placing arsenic trioxide ($As_2O_3$) on the sodium chloride, followed by heating from 100° C. to 1000° C. in an airtight state and then cooling; a third step of separating crystals crystallized in a filter bed; and a fourth step of repeating the second and third steps four to ten times using the crystals obtained in the third step instead of the arsenic trioxide in the second step, thereby obtaining tetraarsenic hexoxide crystals.

A synthesis reactor of a kaolin material and clamps capable of mounting filters thereon above the synthesis reactor are prepared. Then, sodium chloride is placed in the synthesis reactor, and heated and cooled. The reason why sodium chloride is used in the preparation method of the present invention is that when heating is carried out while arsenic trioxide is placed on the sodium chloride in the second step, heat is uniformly transferred to arsenic compounds, thereby helping the sublimation of the arsenic compounds. In order to remove impurities and moisture from such sodium chloride, the sodium chloride is heated at 100-800° C. for 2-6 hours in the first step. In the first step, the sodium chloride is cooled at room temperature for 3-10 hours after the heating.

Then, the second step is conducted by placing arsenic trioxide ($As_2O_3$) on the sodium chloride, followed by heating from 100° C. to 1000° C. in an airtight state and then cooling. Here, after the placing of arsenic trioxide, three to six filters (filter beds) capable of collecting sublimated arsenic are mounted on the clamps such that the intervals between the filters are 2-6 mm. The filters used herein preferably have a basic weight of 70-100 g/m², a thickness of 0.17-0.25 mm, a filtration speed of 22-30 s/100 ml, and a retention rate of 5-10 μm.

After the mounting of the filters, an airtight state was made, and then a bottom portion of the synthesis reactor is heated for 3-10 hours while the temperature is gradationally raised from 100° C. to 1000° C., so that the temperature of the center portion of the highest filter bed is maintained at 150±100° C., and tetraarsenic hexoxide is crystallized passing through the filter beds. Then, cooling is carried out at room temperature for 5 hours or longer, and preferably 5-10 hours.

Then, the third step is conducted by separating white crystals collected in the three to six spaced filter beds installed in a stacked type.

After a small amount of arsenic trioxide remaining on the sodium chloride in the synthesis reactor is removed, the collected white crystals are placed thereon, and then the second and third steps are repeated four to ten times in the same conditions, thereby finally obtaining tetraarsenic hexoxide crystals. As a result of checking the crystal structures obtained according to the preparation method of the present invention, it was verified that most of the crystals were $As_4O_6$-a, which accounted for 99% or more.

The pharmaceutical composition containing a crystalline polymorph of tetraarsenic hexoxide of the present invention can be favorably used in the prevention or treatment of brain cancer.

The pharmaceutical composition of the present invention may be formulated in the form of: an oral formulation, such as a powder, granules, a tablet, a capsule, a suspension, an emulsion, a syrup, or an aerosol; an externally applied preparation; a suppository; and a sterile injectable solution, according to usual methods, respectively. Examples of a carrier, an excipient, and a diluent that may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may be formulated into preparations by using a diluent or an excipient, such as a filler, an extender, a binder, a wetting agent, a disintegrant, or a surfactant. A solid preparation for oral administration includes a tablet, a pill, a powder, granules, a capsule, and the like. These solid preparations may be prepared by mixing the tetraarsenic hexoxide of the present invention with at least one excipient, for example, starch, calcium carbonate, sucrose or lactose, gelatin, or the like. Also, lubricants, such as magnesium stearate and talc, may be used in addition to simple excipients. A liquid preparation for oral administration corresponds to a suspension, a liquid for internal use, an emulsion, a syrup, and the like, and may include simple diluents that are frequently used, such as water and liquid paraffin, and several excipients, such as a wetting agent, a sweetener, an aromatic agent, and a preservative. A preparation for parenteral administration includes a sterile aqueous solution, a non-aqueous solvent, a suspension, an emulsion, a freeze-drying agent, and a suppository. The non-aqueous solvent and the suspension may include propylene glycol, polyethylene glycol, vegetable oils such as olive oil, injectable esters such as ethylolate, and the like. A base material for the suppository may include Witepsol, Macrogol, Tween 61, cacao butter, laurin butter, glycerogelatin, and the like.

The dose of the pharmaceutical composition may vary depending on age, gender, and body weight of a subject to be treated, a particular disease or pathological condition to be treated, severity of a disease or pathological condition, route of administration, and determination of a prescriber. The determination of the dose based on these factors is within the level of a person skilled in the art, and the general dose is in the range of approximately 0.01-500 mg/kg/day. A more preferable dose is 0.1-100 mg/kg/day. The administration may be carried out once a day or several times in a divided dose a day. The above dose is not intended to restrict the scope of the present invention in any way.

The pharmaceutical composition may be administered to mammals, such as rats, domestic animals, and humans, via various routes. All manners of administration may be predicted, and for example, the administration may be carried out through oral, rectal, intravenous, intramuscular, subcutaneous, endometrial, intracerebroventricular injection.

Advantageous Effects

The compositions for prevention or treatment of brain cancer of the present invention have excellent anticancer effects by containing 99% or more of tetraarsenic hexoxide crystalline polymorph a.

Furthermore, the compositions of the present invention were verified to have an excellent effect of inhibiting metastasis of, especially brain cancer, such as brain glioblastoma.

BRIEF DESCRIPTION OF THE DRAWINGS

FIG. 7A shows T2 weighted axial SE images, and FIG. 7B shows post-contrast T1 weighted axial SE images.

FIG. 8A shows T2 weighted SE & FLAIR images and FIG. 8B shows T2 weighted axial SE images.

MODE FOR CARRYING OUT THE INVENTION

Figure 1:
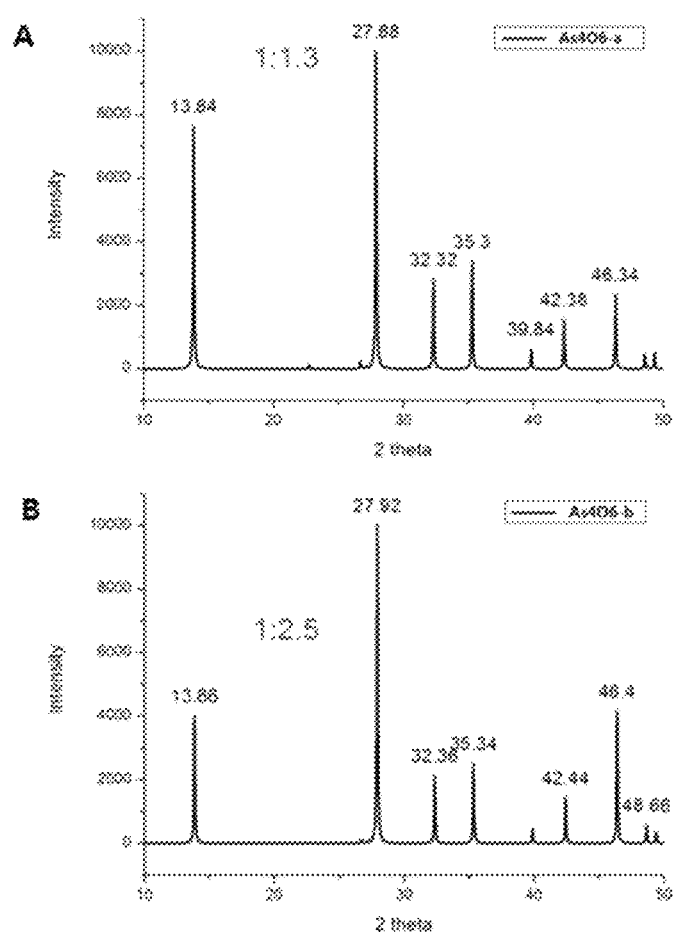
FIG. 1 shows X-ray powder diffraction spectra of $As_4O_6$-a and $As_4O_6$-b.

Hereinafter, preferable examples of the present invention will be described in detail. However, the present invention is not limited to the examples described herein, and thus may be embodied into different forms. Rather, these examples are provided so that this disclosure will be thorough and complete, and will fully convey the scope of the invention to those skilled in the art.

Example 1: Preparation of Present Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m², a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters.

The collected white crystals were placed on the coarse salt inside the synthesis reactor, and the heating, cooling, and crystal collecting processes were again repeated four times, thereby finally obtaining 12.0 g of the crystals. As a result of checking the structure of the obtained arsenic compound crystals, it was confirmed that most of the crystals were $As_4O_6$-a while 99 wt % or more of $As_4O_6$-a and less than 1 wt % of $As_4O_6$-b were obtained.

It was confirmed that as for the differential scanning calorimetry (DSC) value at a temperature rise rate of 10° C./min, $As_4O_6$-a showed an endothermic peak (melting point) at 282.67° C. and $As_4O_6$-b showed an endothermic peak (melting point) at 286.77° C.

X-ray powder diffraction spectra of $As_4O_6$-a and $As_4O_6$-b are shown in FIG. 1, and diffraction data of $As_4O_6$-a and $As_4O_6$-b are shown in Table 2 below.

TABLE 2

| $As_4O_6$-a | | $As_4O_6$-b | |
|---|---|---|---|
| 2θ (°) | Diffraction intensity | 2θ (°) | Diffraction intensity |
| 13.84 | 7631.01 | 13.86 | 4012.09 |
| 27.88 | 10000 | 27.92 | 10000 |
| 32.32 | 2801.74 | 32.36 | 2130.23 |
| 35.3 | 3369.82 | 35.34 | 2511 |
| 39.84 | 623.242 | 39.9 | 447.422 |
| 42.38 | 1551.5 | 42.44 | 1431.86 |
| 46.34 | 2345.2 | 46.4 | 4159.8 |
| 48.6 | 447.69 | 48.66 | 564.995 |
| 49.34 | 502.761 | 49.4 | 375.571 |

As confirmed in FIG. 1 and Table 2, the ratio of main peaks shown at 2θ values of 13.8 and 27.9 was 1:1.3 in $As_4O_6$-a, and the ratio of main peaks shown at 2θ values of 13.8 and 27.9 was 1:2.5 in $As_4O_6$-b. DSC analysis, structure determination, and X-ray diffraction analysis of the prepared compounds were carried out by the following methods.

(1) DSC Analysis

Using a DSC system (SDT Q600 V20.9 Build 20), 20.0 mg of a sample was analyzed while the temperature was raised to 310° C. at a temperature rise rate of 10° C./min with $N_2$ flowing out at 100 mL/min.

(2) X-Ray Crystallography

Single crystals of tetraarsenic hexoxide ($As_4O_6$, MW=395.6) were placed on a glass fiber and then an X-ray beam was applied thereto, to observe diffraction patterns on photographic films and the presence or absence of the organization of diffraction data, thereby determining space groups and cell parameters. Diffraction intensities were collected in the range of 10°<2θ<50°. The crystal structure of $As_4O_6$ was determined from the data by the Patterson method by using a structure determination program (SHELXTL program).

(3) X-Ray Diffractometry

A sample was prepared by pulverizing the obtained crystals into particles having a size of 10-30 μm (−325 mesh), filling a glass holder for X-ray diffraction analysis (20 mm×16 mm×1 mm) with the particles, compressing the particles by a glass slide or the like, and flattening the particles to allow a sample surface to be parallel with a holder surface. The X-ray diffraction spectrum of the crystals was drawn using Cu Kα$_1$ (1.54060 Å) of XRD within a diffraction angle (2θ) of 10° to 50° at a rate of 1°/min (scan step of 0.02°).

Comparative Example 1: Preparation of Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m$^2$, a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters. 48.5 g of crystals were collected from the filters. As a result of checking the crystal structure of the collected arsenic compounds, it was confirmed that $As_4O_6$-b accounted for 99% or more.

Comparative Examples 2 to 4: Preparation of Tetraarsenic Hexoxide

Comparative Examples 2 and 3 were prepared by mixing Example 1 (composition having 99% or more of crystalline polymorph $As_4O_6$-a) and Comparative Example 1 (composition having 99% or more of crystalline polymorph $As_4O_6$-b) at 4:1 and 1:1, respectively.

Test Example 1: Test on Human Glioma Cell Proliferation Inhibitory Effects 1-1. Cell Proliferation Assay (MTT Assay)
(1) Materials and Cell Culture Fetal bovine serum (FBS) and cell culture medium were prepared (Hyclone), and dimethyl sulfoxide (DMSO) and 3-(4,5-dimetyl-thiazol-2yl)-2,5-diphenyltetrazolium bromide (MTT, Amresco LLC, USC) were prepared.

As human cancer cell lines, human brain glioblastoma cell lines U-87MG and U-118MG were obtained from the Shanghai Cell Bank of Chinese Academy of Sciences. The cells were incubated in Eagle's Minimum Essential Medium (EMEM), supplemented with 10% FBS, 100 U/ml penicillin, and 100 μg/ml streptomycin according to the culture condition, in a humidified incubator with 5% $CO_2$ and 95% air. The medium was exchanged every three days.

(2) Cell Proliferation Assay (MTT Assay)

The effects of Example 1 and Comparative Examples 1 to 3 on cell proliferation were assessed using MTT assay. MTT assay is based on the ability of viable cells against MTT to produce insoluble dark blue formazan products. After the cells were suspended in the medium by trypsin treatment and collected, the cells were dispensed at a density of $4 \times 10^3$ cells/well in a 96-well culture dish (Costar, Cambridge, Mass., USA). After 24 hours, Example 1 and Comparative Examples 1 to 3 as treatment samples were added, at 0, 0.625, 1.25, 2.5, 5, 10, 20, 40, or 80 μM, to the cells in the media containing 10% FBS, and then the cells were incubated. Example 1 and Comparative Examples 1 to 3 were dissolved at $5 \times 10^{-+2}$ M in 1 M sodium hydroxide as a stock solution. After the cells were incubated for 48 hours, and 72 hours, MTT assay for cell proliferation was performed, and supernatants were removed at the end of each time interval. Then, 20 μl of 5 mg/mL MTT solution was added per well, and the cells were incubated at 37° C. for 4 hours to form formazan crystals. After the incubation, supernatants were again removed, followed by addition of 100 μl of DMSO to every well, and then mixing was carried out to completely dissolve dark blue crystals. All the crystals were completely dissolved by standing at room temperature for 15 minutes, and the absorbance was measured using a micro-plate reader at a wavelength of 570 nm ($A_{570\ nm}$).

(3) Statistical Analysis

The absorbance value of the control group treated without the sample was calculated as 100, and the absorbance value of the treatment group treated with the sample, compared with that of the control group, was calibrated, and the percentage of inhibition of cell proliferation was calculated according to the following equation.

Percentage (%) of inhibition of cell proliferation=
((mean absorbance of control group cells−mean absorbance of treatment group cells)/mean absorbance of control group cells)×100

All data were expressed as mean±standard error of the mean (mean±SEM). One-way analysis of variance (ANOVA) followed by Dunnett's post-test was used to perform multiple comparison. Statistical significance was defined as $p<0.05$, and each test was repeated three times.

(4) Results of Test Using U-87MG Cell Line

Figure 2:
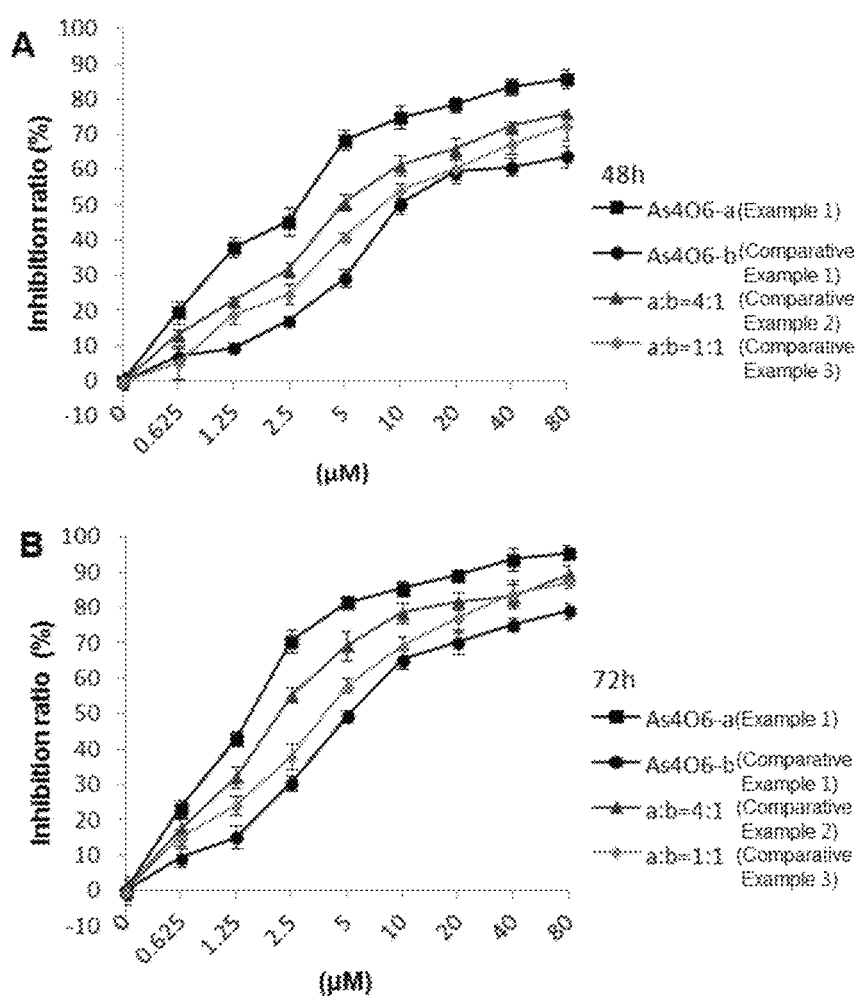
FIG. 2 shows graphs depicting the results of assessing cell proliferation inhibitory effects through MTT assay after the U-87MG cell line was treated with Example 1 and Comparative Examples 1 to 3 and incubated for 48 hours (FIG. 2A) and 72 hours (FIG. 2B).

The human brain glioblastoma cell line U-87MG was treated with Example 1 and Comparative Examples 1 to 3, and incubated for 48 and 72 hours, followed by MTT assay. The results are shown in FIG. 2. It was confirmed that the percentages of inhibition of brain glioblastoma cell proliferation were higher in the treatment with Example 1 and then the incubation for 48 hours (FIG. 2A) and 72 hours (FIG. 2B) compared with the treatment with Comparative Example 1. It was also confirmed that the percentage of inhibition of brain glioblastoma cell proliferation was higher in Example 1 than Comparative Example 2 or 3 in which Example 1 and Comparative Example 1 were mixed at 4:1 or 1:1.

(5) Results of Test Using U-118MG Cells

Figure 3:
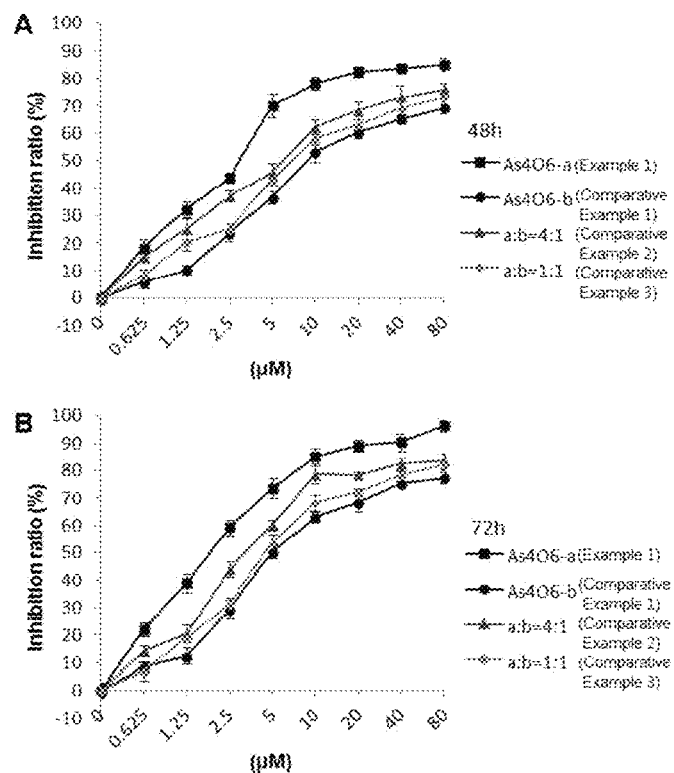
FIG. 3 shows graphs depicting the results of assessing cell proliferation inhibitory effects through MTT assay after the U-118MG cell line was treated with Example 1 and Comparative Examples 1 to 3 and incubated for 48 hours (FIG. 3A) and 72 hours (FIG. 3B).

The human brain glioblastoma cell line U-118MG was treated with Example 1 and Comparative Examples 1 to 3, and incubated for 48 and 72 hours, followed by MTT assay. The results are shown in FIG. 3. It was confirmed that the percentages of inhibition of brain glioblastoma cell proliferation were higher in the treatment with Example 1 and then the incubation for 48 hours (FIG. 3A) and 72 hours (FIG. 3B) compared with the treatment with Comparative Example 1. It was also confirmed that the percentage of inhibition of brain glioblastoma cell proliferation was higher in Example 1 than Comparative Example 2 or 3 in which Example 1 and Comparative Example 1 were mixed at 4:1 or 1:1

Test Example 2: Clinical Test

The following clinical tests were conducted using the composition of Example 1.

(1) Clinical Test-1: 51-Year-Old Female Patient

Figure 4:
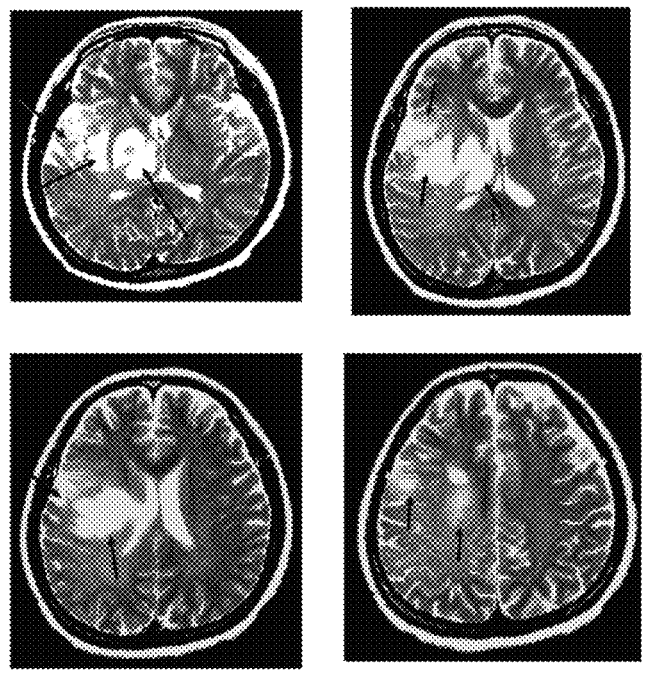
FIG. 4 shows T2 weighted axial SE images as pretreatment MRI images of a patient (Clinical Test-1) diagnosed with gliomatosis cerebri.
Figure 5:
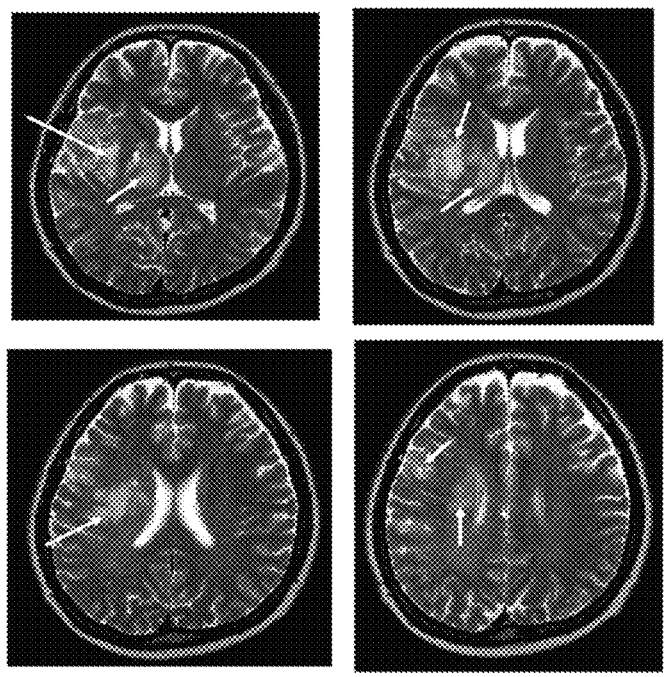
FIG. 5 shows T2 weighted axial SE images as MRI images showing that tumor sizes were reduced after two months of radiotherapy together with administration of Example 1 on the patient with gliomatosis cerebri in Clinical Test-1.
Figure 6:
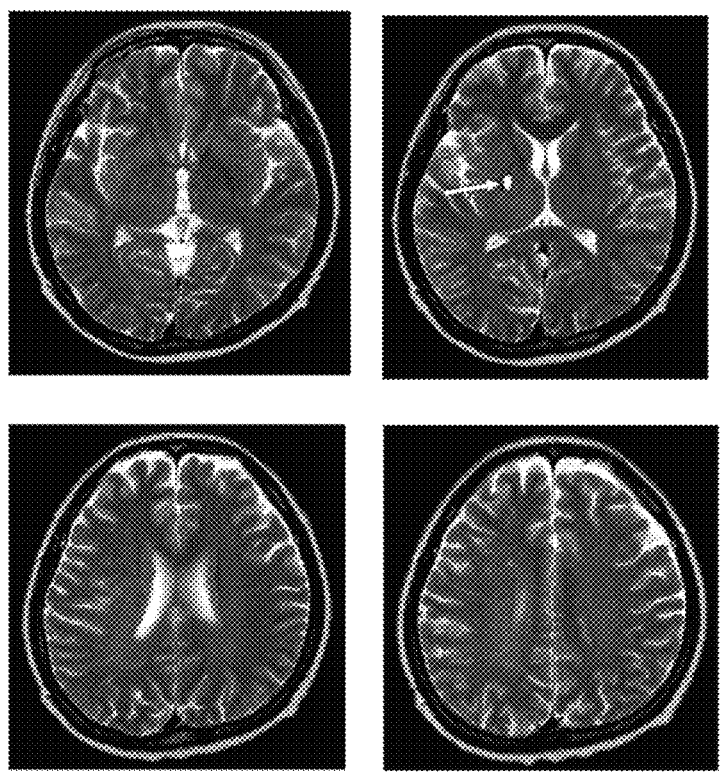
FIG. 6 shows T2 weighted axial SE images as MRI images showing that tumors almost disappeared after three months of radiotherapy together with administration of Example 1 on the patient with gliomatosis cerebri in Clinical Test-1.

This female patient had no subjective symptoms, but had a brain lesion found in a health checkup, and was diagnosed with gliomatosis cerebri (pathologic diagnosis: anatomic astrocytomas) in a brain biopsy at the Seoul National University Hospital. From the 10th day after the diagnosis, mobility weakening and trembling symptoms of both arms began to appear and then proceeded rapidly. Example 1 was administered at a dose of 15 mg per day from the 17th day after the diagnosis, and the mobility weakening and trembling symptoms began to improve. Radiotherapy was together performed from the 27th day to the 75th day after the diagnosis, and thereafter the symptoms disappeared completely. Pre-treatment MRI images of this patient are shown in FIG. 4, and MRI images after two months and three months of radiotherapy together with administration of Example 1 are shown in FIGS. 5 and 6, respectively.

(2) Clinical Test-2: 16-Year-Old Female Patient

Figure 7:
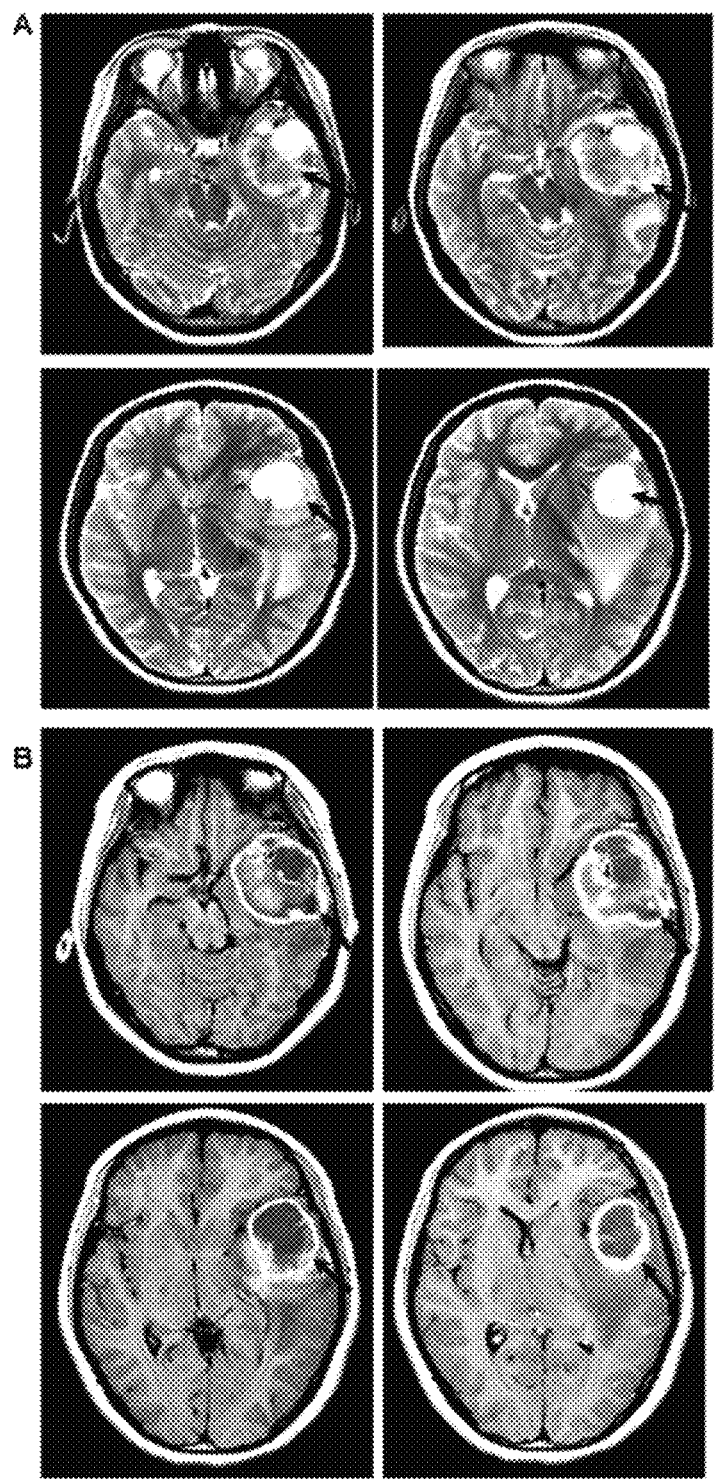
FIG. 7 shows pre-treatment MRI images of a patient diagnosed with glioblastoma in the left parieto-temporal lobe (Clinical Test-2).
Figure 8:
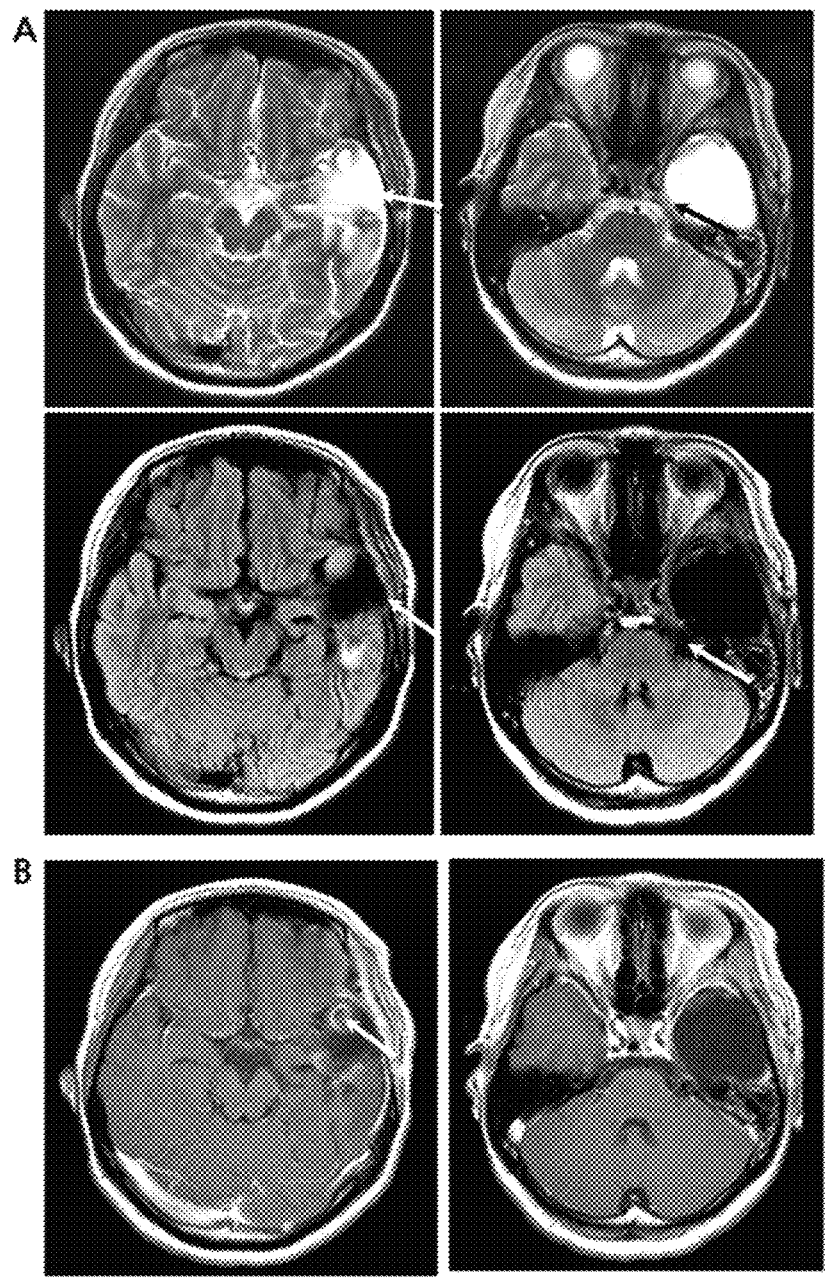
FIG. 8 shows MRI images after surgery and radiotherapy on the patient with glioblastoma in Clinical Test-2.
Figure 9:
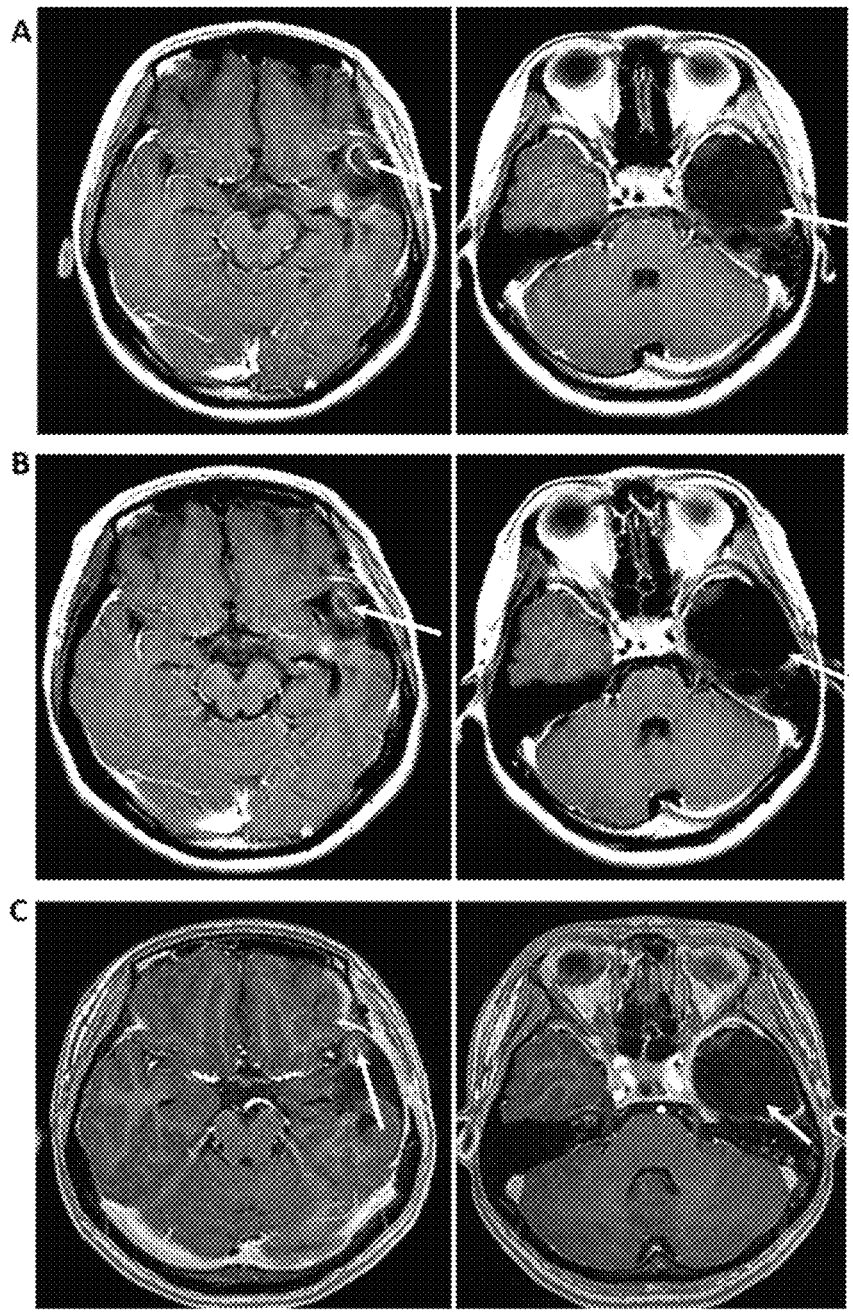
FIG. 9 shows T1 weighted axial SE images as MRI images after four months (FIG. 9A), seven months (FIG. 9B), and ten months (FIG. 9C) of administration of Example 1 on the patient with glioblastoma in Clinical Test-2.

This patient with symptoms of headache, vomiting, diplopia, and visual field defect was diagnosed with glioblastoma in the left parieto-temporal lobe. On the 3rd day after the diagnosis, tumor removal was conducted by surgery, and the tumor was confirmed as glioblastoma of the WHO grade IV/IV as a result of pathologic diagnosis. Radiotherapy with Tremodal treatment (61.2 Gy/33fx) was performed from the 45th day to the 90th day after the diagnosis. The remaining tumors were still confirmed on MRI images after the radiotherapy and Tremodal treatment. From the 95th day after the diagnosis, 5 mg of Example 1 was administered three times a day for 17 months. The patient had no subjective symptom from 2 months of administration of Example 1, and the sizes of remaining tumors were confirmed to decrease after the administration of Example 1. The pre-treatment MRI images of this patient are shown in FIG. 7, and MRI images after the surgery and radiotherapy are shown in FIG. 8. Respective images after four months, seven months, and ten months of administration of Example 1 are shown in FIGS. 9A, 9B, and 9C, respectively.

It was confirmed through the clinical test results that the composition of the present invention had effects of effectively inhibiting the proliferation of malignant brain tumors, such as glioblastoma, by passing through the brain-blood barrier (BBB).

Test Example 3: In Vivo Efficacy Test in Animal Models Transplanted with Human Brain Glioblastoma Cell Line (1) Methods The human brain glioblastoma cell line U-87MG (purchased from ATCC) was incubated in Eagle's Minimum Essential Medium (EMEM) supplemented with 10% FBS, 100 U/ml penicillin, and 100 μg/ml streptomycin in an incubator under conditions of 37° C., 5% $CO_2$, and 95% air. The medium was exchanged every three days.

The U-87MG cells labeled with luciferase were inoculated into the primary site of the brain in 15 Balb/C female nude mice weighing 16-19 g, and the amount of cells inoculated was $5×10^5$/5 uL. The animals were subjected to imaging examinations on the 6th day after the inoculation, when the surgical sites of the animals were restored and the tumor cells were slightly grown. The animals were randomly divided into two groups, four animals for each group, according to the imaging results. A test group was administered with a solution containing Example 1 dissolved in physiological saline (0.9% NaCl), and a control group was administered with only physiological saline, which is a solvent used for the test group. The animals of the two groups were administered once daily with physiological saline or 2.25 mg/kg Example 1. The dose was 10 uL/g on the basis of the weight of the animals. During the administration, the weight and health conditions of the animals were continuously monitored, and at the same time, the animals were subjected to image examination. Animals with excessively reduced weights (>20%) or unhealthy conditions were euthanized, and then tumors were removed, fixed with formalin, and subjected to a biopsy.

(2) Weight Measurement Results

After 9 days of drug administration, the animals of the test group showed an almost unchanged weight, but the animals of the control group showed a largely reduced weight as shown below.

TABLE 3

| Group | Number of animals | Weight (g)[a] Before administration | 9 days after the first administration | $p^b$ | Body change 9 days after the first administration (g) |
|---|---|---|---|---|---|
| Control group (physiological saline administration) | 4 | 16.4 ± 0.2 | 14.7 ± 0.8 | — | −1.7 |
| Test group (Example 1 administration) | 4 | 16.9 ± 0.2 | 16.1 ± 0.5 | 0.14 | −0.8 |

[a]Mean ± SEM
[b]Statistical comparison t-test being performed for weight of test group and weight of control group after 9 days of administration.

During the test, the animals of the control group showed a remarkably reduced weight over 15 days after the inoculation of cells, and the animals began to die at the 17-19 days after the inoculation of cells.

(3) Results of Tumor Imaging Signal Inhibition

Figure 10:
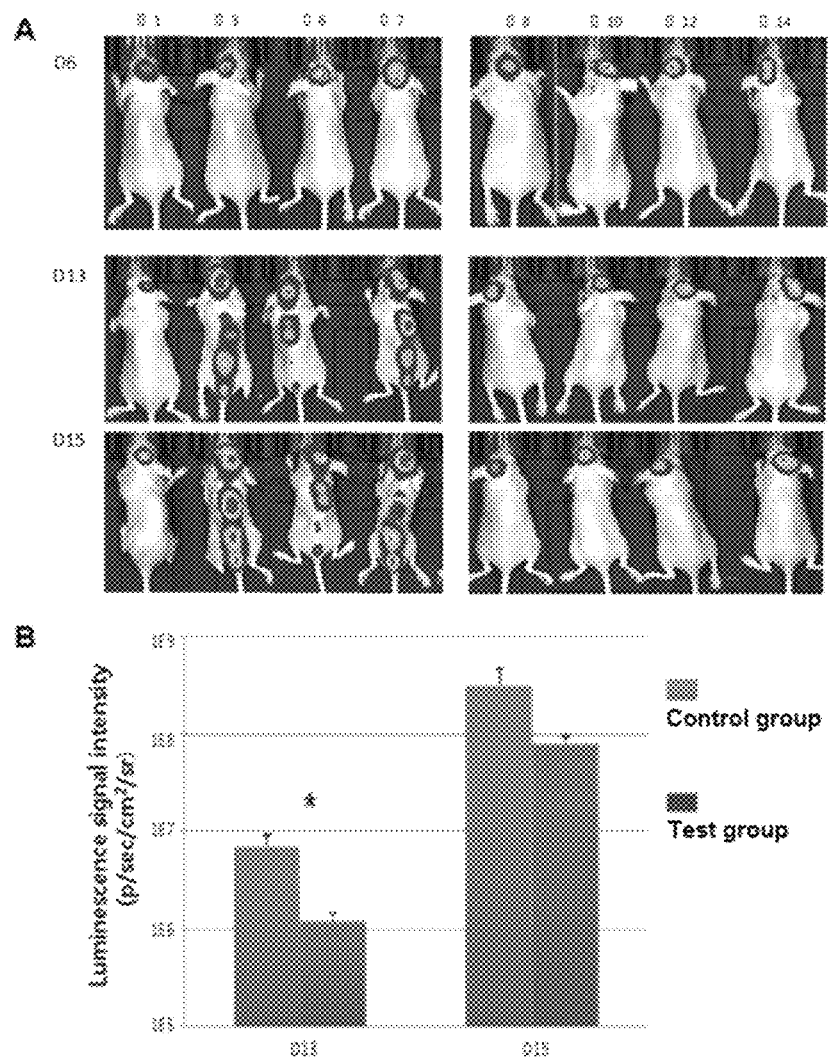
FIG. 10 shows images (FIG. 10A) and a graph (FIG. 10B) depicting tumor imaging signal inhibitory effects after U-87MG cell line was inoculated into Balb/C female nude mice.

As a result of investigating the results of tumor imaging signal inhibition, as shown in FIG. 10A, the animals of the control group showed strong tumor signal intensities from the 7th day of administration (the 13th after the inoculation), and the tumor signals were observed to be distributed in the spine due to tumor metastasis into the spine, while the tumor signals of the animals of the test group were hardly observed in the spine, and the intensities thereof were also significantly light. As confirmed in FIG. 10B, it was confirmed through the comparison of biological imaging results at the 7th and 9th days of administration (on 13 and 15 days after the inoculation) between the control group and the test group that the luminescence signal intensities due to the proliferation and metastasis of tumors in the control group were much stronger than those in the test group.

The invention claimed is:

1. A pharmaceutical composition containing tetraarsenic hexoxide ($As_4O_6$) as an active ingredient for prevention or treatment of brain cancer, wherein the tetraarsenic hexoxide includes 99 wt % or more of tetraarsenic hexoxide crystalline polymorph a having features (i) to (iii) below:
   (i) Cell parameters:
   a=b=c=11.0734 Å
   α=β=γ=90°
   V=1357.82 Å$^3$
   (ii) As—O bond length: 1.786 Å
   (iii) O—As—O bond angle: 98.36°.

2. The pharmaceutical composition of claim 1, wherein the tetraarsenic hexoxide has a purity of 99.9% or higher.

3. The pharmaceutical composition of claim 1, wherein in the X-ray powder diffraction spectrum of the crystalline polymorph a, obtained by using a light source wavelength of 1.5406 Å within a diffraction angle (2θ) of 10° to 50° at a rate of 1°/min (scan step of 0.02°), peaks are shown at 2θ values of 13.84, 27.88, 32.32, 35.3, 39.84, 42.38, 46.34, 48.6, and 49.34.

4. A pharmaceutical composition containing tetraarsenic hexoxide ($As_4O_6$) as an active ingredient for inhibition of brain cancer metastasis, wherein the tetraarsenic hexoxide includes 99 wt % or more of tetraarsenic hexoxide crystalline polymorph a having features (i) to (iii) below:
   (i) Cell parameters:
   a=b=c=11.0734 Å
   α=β=γ=90°
   V=1357.82 Å$^3$
   (ii) As—O bond length: 1.786 Å
   (iii) O—As—O bond angle: 98.36°.

5. A method for preparing the pharmaceutical composition containing tetraarsenic hexoxide ($As_4O_6$) for prevention or treatment of brain cancer of claim 1, the method comprising:
   a first step of heating sodium chloride at 100~800° C., followed by cooling;
   a second step of placing arsenic trioxide ($As_2O_3$) on the sodium chloride, followed by heating from 100° C. to 1000° C. in an airtight state and then cooling;
   a third step of separating crystals crystallized in a filter bed; and
   a fourth step of repeating the second and third steps four to ten times using the crystals obtained in the third step instead of the arsenic trioxide in the second step, thereby obtaining tetraarsenic hexoxide crystals,
   wherein the tetraarsenic hexoxide crystals obtained in the fourth step include 99 wt % or more of tetraarsenic hexoxide crystalline polymorph a ($As_4O_6$-a).

* * * * *